(12) United States Patent
Ting et al.

(10) Patent No.: US 9,905,780 B2
(45) Date of Patent: Feb. 27, 2018

(54) ORGANIC ELECTROLUMINESCENT MATERIALS CONTAINING N-PHENYLCARBOLINE AND ORGANIC ELECTROLUMINESCENT DEVICE BY USING THE SAME

(71) Applicant: Yuan Ze University, Chung-Li (TW)

(72) Inventors: Pei-Ling Ting, Chung-Li (TW); Man-Kit Leung, Chung-Li (TW); Tien-Lung Chiu, Chung-Li (TW); Jiun-Haw Lee, Chung-Li (TW); Lik-Ka Yun, Chung-Li (TW)

(73) Assignee: YUAN ZE UNIVERSITY, Chung-Li (TW)

( * ) Notice: Subject to any disclaimer, the term of this patent is extended or adjusted under 35 U.S.C. 154(b) by 232 days.

(21) Appl. No.: 14/986,359

(22) Filed: Dec. 31, 2015

(65) Prior Publication Data

US 2017/0162794 A1 Jun. 8, 2017

(30) Foreign Application Priority Data

Dec. 4, 2015 (TW) .............................. 104140798 A (51) Int. Cl.
*H01L 51/50* (2006.01)
*H01L 51/00* (2006.01)
(Continued)

(52) U.S. Cl.
CPC ........ *H01L 51/0072* (2013.01); *C07D 471/04* (2013.01); *C09K 11/02* (2013.01);
(Continued)

(58) Field of Classification Search
None
See application file for complete search history.

(56) References Cited

U.S. PATENT DOCUMENTS

2008/0230747 A1* 9/2008 Nomura .............. C07D 413/10
252/301.16

FOREIGN PATENT DOCUMENTS

KR 10-2012-0072787 * 7/2012 ............. C09K 11/06

* cited by examiner

*Primary Examiner* — Gregory Clark
(74) *Attorney, Agent, or Firm* — Muncy, Geissler, Olds & Lowe, P.C.

(57) ABSTRACT

An organic electroluminescent material is shown in General Formula (1),

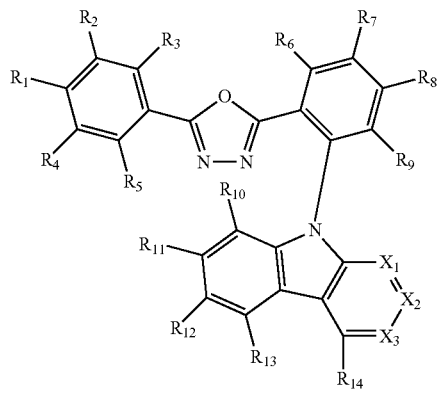

General Formula (1)

wherein one of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

12 Claims, 1 Drawing Sheet

(51) Int. Cl.
*C09K 11/06* (2006.01)
*C09K 11/02* (2006.01)
*C07D 471/04* (2006.01)

(52) U.S. Cl.
CPC ............ *C09K 11/06* (2013.01); *H01L 51/007* (2013.01); *C09K 2211/1007* (2013.01); *C09K 2211/1029* (2013.01); *C09K 2211/1048* (2013.01); *C09K 2211/185* (2013.01); *H01L 51/5004* (2013.01); *H01L 51/5016* (2013.01); *H01L 2051/0063* (2013.01); *H01L 2251/552* (2013.01)

ORGANIC ELECTROLUMINESCENT MATERIALS CONTAINING N-PHENYLCARBOLINE AND ORGANIC ELECTROLUMINESCENT DEVICE BY USING THE SAME

CROSS REFERENCE TO RELATED APPLICATIONS

This Non-provisional application claims priority under 35 U.S.C. § 119(a) on Patent Application No(s). 104140798 filed in Taiwan, Republic of China on Dec. 4, 2015, the entire contents of which are hereby incorporated by reference.

BACKGROUND OF THE INVENTION

Technical Field

The present invention relates to an organic electroluminescent material and an organic electroluminescent device and, in particular, to an organic electroluminescent material containing N-phenylcarboline and an organic electroluminescent device.

Related Art

With the advances in electronic technology, a light weight and high efficiency flat display device has been developed. An organic electroluminescent display possibly becomes the mainstream of the next generation flat panel display device due to its advantages of self-luminosity, no restriction on viewing angle, power conservation, simple manufacturing process, low cost, high response speed, full color and so on.

In general, an organic electroluminescent device includes an anode, an organic luminescent layer and a cathode. When a direct current is provided for the organic electroluminescent device, electron holes and electrons flow into the organic luminescent layer respectively through the anode and the cathode. Charge carriers move, meet, and then recombine in the organic luminescent layer because of the potential difference caused by an applied electric field. The excitons generated by the recombination of the electrons and the electron holes may excite the luminescent molecules in the organic luminescent layer. The excited luminescent molecules then release the energy in the form of light.

Nowadays, organic electroluminescent displays usually adopt host-guest emitter systems. The organic luminescent layer disposed therein includes a host material and a guest material. Electron holes and electrons transmit to the host material to perform recombination and then generate energy. The guest material can be categorized into fluorescent material and phosphorescent material. Theoretically, the internal quantum efficiency can approach 100% by using appropriate phosphorescent material. Therefore, the phosphorescent material recently have become one of the most important developments in the field of organic electroluminescent materials.

In the development of blue host material, the triplet energy gap of the host material must be higher than or equal to that of the guest material to avoid the energy lost caused by back energy transfer. The energy lost can result in low luminous efficiency (i.e., low current efficiency) and short emission lifetime. Therefore, it is necessary for the host material to have greater triplet energy gap. In order to increase the triple energy gap of the blue host material, much research has been focused on the single benzene ring with various ortho-substituted groups. In ortho-substitution with electron-transporting group (e.g., OXD or TAZ) and hole-transporting group (e.g., Cbz), a dipole molecule is created by breaking π-conjugated molecules due to steric hindrance.

Besides, the selection of organic electroluminescent material is not only based on the matching energy gap but also the high temperature of decomposition to avoid pyrolysis caused by high temperature and also avoid the resulted decreasing of stability.

Accordingly, the present invention is provided an organic electroluminescent material containing N-phenylcarboline and an organic electroluminescent device which has high triplet energy gap and fine heat stability.

SUMMARY OF THE INVENTION

In view of the foregoing objectives, the invention provides an organic electroluminescent material containing N-phenylcarboline and an organic electroluminescent device by using the same. The organic electroluminescent material has high triplet energy gap and fine heat stability.

An organic electroluminescent material according to the present invention has a structure of the following General Formula (1).

General Formula (1)

One of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

In one embodiment, X1 is a nitrogen atom, X2 and X3 are both independent carbon atoms, and R1 to R14 are all independent hydrogen atoms.

In one embodiment, X2 is a nitrogen atom, X1 and X3 are both independent carbon atoms, and R1 to R14 are all independent hydrogen atoms.

In one embodiment, X3 is a nitrogen atom, X1 and X2 are both independent carbon atoms, and R1 to R14 are all independent hydrogen atoms.

An organic electroluminescent device which is also provided includes a first electrode layer, a second electrode layer, and an organic luminescent unit. The organic luminescent unit is disposed between the first electrode layer and the second electrode layer. The organic luminescent unit has at least an organic luminescent material as shown in General Formula (1).

General Formula (1)

One of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the organic luminescent unit comprises an organic luminescent layer.

In one embodiment, the organic luminescent unit further comprises a hole transport layer and an electron transport layer, and the organic luminescent layer is disposed between the hole transport layer and the electron transport layer.

In one embodiment, the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

In one embodiment, the organic luminescent layer comprises a host material and a guest material. The host material is the organic electroluminescent layer and the guest material is a phosphorescent material.

In one embodiment, the content of host material in organic luminescent layer is between 60 vol % to 95 vol %.

In one embodiment, the content of guest material in organic luminescent layer is between 5 vol % to 40 vol %.

In summary, the organic electroluminescent materials containing N-phenylcarboline and the organic electroluminescent device by using the same are based on the N-phenylcarboline group and the oxadiazole group. In addition, the N-phenylcarboline group is undergone single nitrogen-substituted heterocyclic ring modification and the positions of the nitrogen-substitution are various. Therefore, the phosphorescent bipolar host materials, such as 1-CbOXD, 2-CbOXD, and 3-CbOXD, are synthesized accordingly. In the present invention, the carboline group is functioned as a hole-transporting group, and the oxadiazole group is functioned as an electron-transporting group, and the hole-transporting group is undergone single nitrogen-substituted heterocyclic ring modification. Therefore, the phosphorescent bipolar host materials are synthesized accordingly. Such phosphorescent dipolar host materials and the organic light-emitting diodes comprising such materials will have high luminous efficiency.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

Organic Electroluminescent Material

An organic electroluminescent material according to the first embodiment of the present invention has a structure of the following General Formula (1).

General Formula (1)

One of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

The organic electroluminescent material of General Formula (1) according to the embodiment can be the host material of the organic luminescent layer in an organic electroluminescent device. A preferred example is the compound of Chemical Formula (1), 1-CbOXD, where X1 is a nitrogen atom, X2 and X3 are both independent carbon atoms, and R1 to R14 are all independent hydrogen atoms.

Chemical Formula (1)

Alternatively, another preferred example is the compound of Chemical Formula (2), 2-CbOXD, where X2 is a nitrogen atom, X1 and X3 are both independent carbon atoms, and R1 to R14 are all independent hydrogen atoms.

Chemical Formula (2)

Still another preferred example is the compound of Chemical Formula (3), 3-CbOXD, where X3 is a nitrogen atom, X1 and X2 are both independent carbon atoms, and R1 to R14 are all independent hydrogen atoms.

Chemical Formula (3)

In the present embodiment, the compound having the structure of General Formula (1) uses the N-phenylcarboline group as a hole-transporting group and uses the oxadiazole group as an electron-transporting group. In addition, the hole-transporting group (i.e., N-phenylcarboline group) is undergone single nitrogen-substituted heterocyclic ring modification. Therefore, the phosphorescent bipolar host materials are synthesized accordingly. Such phosphorescent bipolar host materials and the organic light-emitting diodes comprising such materials will have high luminous efficiency. In other words, the host materials according to the above-mentioned embodiment comprises an electron-transporting group and a hole-transporting group in single molecule and has a characteristic of bipolar carrier-transporting.

Furthermore, the guest materials for use with the host materials described in the embodiment may be any suitable luminescent materials applied to the organic luminescent layer of the organic electroluminescent device, for example but not limited to, Ir(2-phq)$_3$, Ir(ppy)$_3$, and Flrpic, and their structures are respectively shown as the following Chemical Formula (4), Chemical Formula (5), and Chemical Formula (6).

Chemical Formula (4)

Chemical Formula (5)

Chemical Formula (6)

Moreover, the material having the structure of General Formula (1), in addition to being applied in the organic luminescent layer, can also be applied in any layer of an organic electroluminescent unit, for example, a hole injection layer, hole transport layer, electron blocking layer, electron transport layer, or electron injection layer.

Organic Electroluminescent Device

Figure 1:
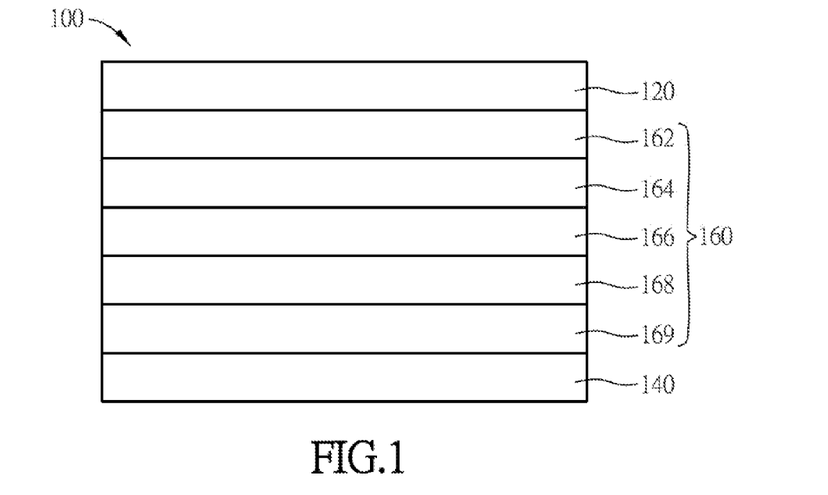
FIG. 1 is a schematic diagram of an organic electroluminescent device of the second embodiment according to the invention.

Referring to FIG. 1, it is a schematic diagram of an organic electroluminescent device of the third embodiment according to the invention. The organic electroluminescent device 100 of the embodiment includes a first electrode layer 120, a second electrode layer 140, and an organic luminescent unit 160. In the embodiment, the first electrode layer 120 can be a transparent electrode material, such as indium tin oxide (ITO), and the second electrode layer 140 may be a metal, transparent conductive substance, or any other suitable conductive material. On the other hand, the first electrode layer 120 can be may be a metal, transparent conductive substance, or any other suitable conductive material, and the second electrode layer 140 may be a transparent electrode material. Overall, at least one of the first electrode layer 120 and the second electrode layer 140 of the embodiment is a transparent electrode material, so that the light emitted from the organic luminescent unit 23 may pass through the transparent electrode, thereby enabling the organic electroluminescent device 100 to emit light.

In addition, please also refer to FIG. 1, the organic luminescent unit 160 can comprise a hole transport layer 162, electron blocking layer 164, organic luminescent layer 166, electron transport layer 168, and electron injection layer 169. The electron blocking layer 164, the organic luminescent layer 166 and the electron transport layer 168 are sequentially disposed between the hole transport layer 162 and the electron injection layer 169.

The material of the hole transport layer 162 may be 1,1-Bis[4-[N,N'-di(p-tolyl)amino]phenyl]cyclohexane (TAPC), N,N-bis-(1-naphthyl)-N,N-diphenyl-1,1-biphenyl-4,4-diamine (NPB), or N-N'-diphenyl-N-N'bis(3-methylphenyl)-[1-1'-biphenyl]-4-4'-diamine (TPD). Moreover, the thickness of the hole transport layer 162 of the embodiment is in the range of, for example,0.1 nm to 100 nm. The hole transport layer 162 may facilitate the electron hole to be transported from the first electrode layer 120 to the organic luminescent layer 166 in order to increase the transport rate of the electron hole, and also to reduce the driving voltage of the organic electroluminescent device 100.

The material of the electron blocking layer 164 may be N,N'-dicarbazolyl-3,5-benzene (mCP) or any other material with low electron affinity. In the embodiment, the thickness of the electron blocking layer 164 is in the range of, for example, 0.1 nm to 30 nm. The electron blocking layer 164 may further increase the transport rate of the electron hole from the hole transport layer 162 to the organic luminescent layer 166.

The thickness of the organic luminescent layer 166 of the embodiment is between 5 nm and 60 nm, the organic luminescent layer 166 includes the host material and the guest material, and the host material can be the above mentioned organic electroluminescent material which has a structure of the following General Formula (1).

General Formula (1)

One of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

A preferred example is the compound of Chemical Formula (1), 1-CbOXD, where X1 is a nitrogen atom, X2 and X3 are both independent carbon atoms, and R1 to R14 are all independent hydrogen atoms.

Chemical Formula (1)

Alternatively, another preferred example is the compound of Chemical Formula (2), 2-CbOXD, where X2 is a nitrogen atom, X1 and X3 are both independent carbon atoms, and R1 to R14 are all independent hydrogen atoms.

Chemical Formula (2)

Still another preferred example is the compound of Chemical Formula (3), 3-CbOXD, where X3 is a nitrogen atom, X2 and X3 are both independent carbon atoms, and R1 to R14 are all independent hydrogen atoms.

Chemical Formula (3)

In one embodiment, the content of host material in organic luminescent layer is between 60 vol % to 95 vol %. Moreover, the content of guest material in organic luminescent layer is between 5 vol % to 40 vol %.

Furthermore, the guest materials may be any suitable luminescent materials applied to the organic luminescent layer of the organic electroluminescent device, for example but not limited to, $Ir(2-phq)_3$, $Ir(ppy)_3$, and FIrpic, and their structures are respectively shown as the following Chemical Formula (4), Chemical Formula (5), and Chemical Formula (6).

Chemical Formula (4)

Chemical Formula (5)

In addition, the material of the electron transport layer 168 may be, but not Chemical Formula (6) limited to, a metal complex, such as Tris-(8-hydroxy-quinoline)aluminum ($Alq_3$) and bis(10-hydroxybenzo-[h]quinolinato)beryllium ($BeBq_2$), or a heterocyclic compound, such as 2-(4-Biphenylyl)-5-(4-tert-butylphenyl)-1,3,4-oxadiazole (PBD), 3-(4-Biphenylyl)-4-phenyl-5-tert-butylphenyl-1,2,4-triazole (TAZ), 2,2', 2''-(1,3,5 -Benzinetriyl)-tris(1-phenyl-1-H-benzimidazole) (TPBI), diphenylbis(4-(pyridin-3-yl)phenyl)silane (DPPS), and 3,3'-[5'-[3-(3-Pyridinyl)phenyl][1,1':3,3''-diyl]bispyridine (TmPyPB). In the embodiment, the thickness of the electron transport layer 168 may be between 0.1 nm and 100 nm. The electron transport layer 168 may improve the velocity of the electron being transported from the second electrode layer 140 to the organic luminescent layer 166. Moreover, the material of the electron injection layer 169 may be, for example, LiF. The thickness of the electron injection layer 169 may be, for example, 0.9 nm.

Figure 2:
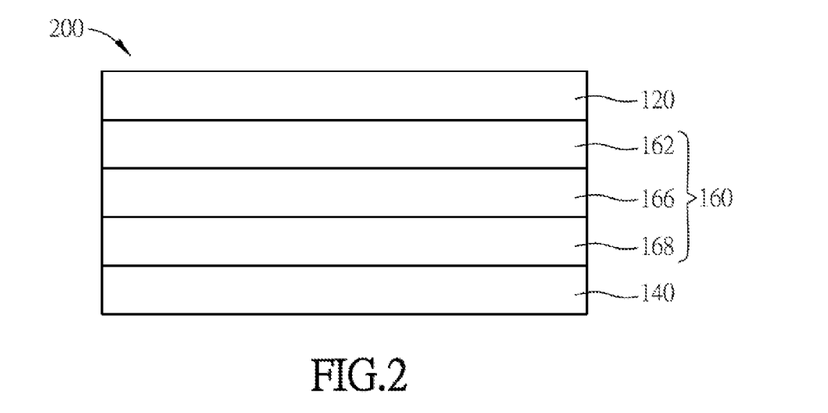
FIG. 2 is a schematic diagram of an organic electroluminescent device of the third embodiment according to the invention.

In addition, FIG. 2 is a schematic diagram of an organic electroluminescent device 200 of the third embodiment according to the invention. The configuration of the organic electroluminescent device 200 is substantially similar with that of the organic electroluminescent device 100, and same elements have substantial the same characteristics and functions. Therefore, the similar references relate to the similar elements, and detailed explanation is omitted hereinafter.

Please refer to FIG. 2, in the embodiment, the organic luminescent unit 160 can comprise a hole transport layer 162, organic luminescent layer 166, and electron transport layer 168. The organic luminescent layer 166 is disposed between the hole transport layer 162 and the electron transport layer 168.

Figure 3:
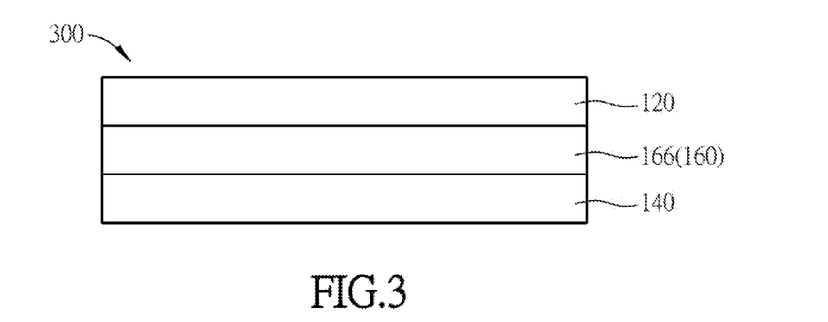
FIG. 3 is a schematic diagram of an organic electroluminescent device of the fourth embodiment according to the invention.

In addition, FIG. 3 is a schematic diagram of an organic electroluminescent device 300 of the fourth embodiment according to the invention. The configuration of the organic electroluminescent device 300 is substantially similar with that of the organic electroluminescent device 100, and same elements have substantial the same characteristics and functions. Therefore, the similar references relate to the similar elements, and detailed explanation is omitted hereinafter.

Please refer to FIG. 3, in the embodiment, the organic luminescent unit 160 can comprise an organic luminescent layer 166.

In addition, the configuration of the organic electroluminescent device according to the invention is not limited to what is disclosed in the second, third, or fourth embodiment. The second, third, and fourth embodiments are embodiments for illustration.

In order to illustrate the synthesis of Chemical Formula (1) to Chemical Formula (3), there are several examples shown below. The products synthesized according to the following examples are examined by $^1$H-NMR, $^{13}$C-NMR, mass spectrometry, and elemental analysis.

EXAMPLE A

Preparation of 2-(2-bromophenyl)-5-phenyl-1,3,4-oxadiazole

Sodium azide (20.0 g, 307.9 mmol) and ammonium chloride (16.8 g, 314.5 mmol) were placed into a double neck flask (500 mL) with a magnetic stir bar, and benonitrile (15.70 mL, 152.3 mmol) and dimethylformamide (160.00 mL) were injected under argon atmosphere. The mixture was heated to 125° C. and refluxed for 24 hours, followed by cooling to room temperature. The solvent was removed by vacuum distillation. Subsequently, deionized water (80.00 mL) was added and a large amount of white precipitates was formed. Hydrochloric acid was added slowly by drops to quench the remaining sodium azide. At the same time, a large amount of highly toxic hydrazoic acid was generated. After stirred for 24 hours at room temperature, a crystalized solid substance may be observed at the bottom of the flask. If no such crystalized solid substance are formed, it can be filtered by suction to collect the white solid and recrystallized with EtOH. The soild was washed by acetone and filtered by suction. The solvent was removed by vaccum distillation and the compound 7 of white acicular crystalized solid was obtained (21.32 g), and the yield is 94.8%. Spectral data as follow: $^1$H NMR (400 MHz, d$_6$-DMSO) : δ 8.04-8.02 (m, 2H), 7.59-7.58 (m, 3H); $^{13}$C NMR (100 MHz, d$_6$-DMSO) : δ 131.04, 129.21, 126.74. The reaction was shown as the following Equation (1).

Equation (1)

Next, the compound 7 of white acicular crystalized solid (10.0 g , 69.4 mmol) was placed into a double neck flask (250.00 mL), and dry pyridine (104.00 mL) and 2-bromobenzoyl chloride (7.77 mL, 59.3 mmol) were injected under argon atmosphere. The mixture was heated to 90° C. and refluxed for 24 hours, followed by re-precipitated by diluted hydrochloric acid. A large amount of white precipitates was formed. The solid was filtered by suction and recrystallized by acetone. After washed by methyl alcohol, a compound 8 of white crystal (i.e., 2-(2-bromophenyl)-5-phenyl-1,3,4-oxadiazole, 16.5 g) was obtained, and the yield is 80%. Spectral data as follow: $^1$H NMR (400 MHz, d$_6$-DMSO) : δ 8.08-8.05 (m, 3H), 7.90-7.88 (m, 1H), 7.67-7.54 (m, 5H) ; $^{13}$C NMR (100 MHz, d$_6$-DMSO) : δ 163.14, 161.18, 141.53, 138.74, 136.62, 133.51, 131.58, 131.54, 130.65, 129.88, 128.75, 128.63, 128.16, 125.50, 121.89, 114.53, 109.58. The reaction was shown as the following Equation (2).

Equation (2)

EXAMPLE B

Preparation of alpha-carboline

Firstly, 2, 3-Dichloropyridine (2.96 g, 20.0 mmol), palladium(II) acetate (220.0 mg, 1.0 mmol), triphenylphosphine (520.0 mg, 2.0 mmol), and sodium tert-butoxide (2.30 g, 24.0 mmole) were placed into a double and wide neck flask (100mL) with a magnetic stir bar, and o-xylene (50.00 mL) and aniline (1.86 mL, 22.0 mmol) were injected through a needle with dual tips under argon atmosphere. The o-xylene and aniline were dewatered and deoxygenated in advance. The mixture was heated to 120° C. and refluxed for 24 hours, followed by cooling to room temperature. The mixture was filtered through celite and the solvent was removed by vacuum distillation. After purified by column chromatography and eluted by the solution of dichloromethane and n-hexane (1:5 in v/v), the compound 1 (3.22 g) of light yellow oil was obtained, and the yield is 78.7%. Spectral data as follow: $^1$H NMR (400 MHz, $d_6$-DMSO) : δ 8.33 (s, 1H), 8.09 (d, J=4.8 Hz, 1H), 7.76 (d, J=7.6 Hz, 1H), 7.68 (d, J=8.4 Hz, 2H), 7.28 (t, J=7.6 Hz, 2H), 7.00-6.96 (m, 1H), 6.82-6.79 (m, 1H) ; $^{13}$C NMR (100 MHz, $d_6$-DMSO) : δ 152.05, 146.27, 141.09, 138.02, 128.96, 122.68, 121.23, 116.34, 116.16. The reaction was shown as the following Equation (3).

Equation (3)

Next, the compound 1 (3.22 g, 15.7 mmol), palladium(II) acetate (220.0 mg, 1.0 mmol), and tricyclohexylphosphine tetrafluoroborate (740.0 mg, 2.0 mmol) were placed in a double neck flask, and N,N-dimethylacetaminde (50.00 mL) and 1,8-diazabicycloundec-7-ene (0.71 mL, 4.0 mmol) were injected through a needle with dual tips under argon atmosphere. The mixture was heated to 165° C. and refluxed for 24 hours, followed by cooling to room temperature. The mixture was filtered through celite and washed with ethyl acetate. The solvent was removed by vacuum distillation. After purified by the column chromatography and eluted by the solution of n-hexane and ethyl acetate (v/v in 4:1), the compound 2 (i.e., alpha-carboline, 1.265 g) of yellow solid was obtained, and the yield is 48%. Spectral data as follow: $^1$H NMR (400 MHz, $d_6$-DMSO) : δ 11.82 (s, 1H), 8.48 (dd, J=1.2, 1.6 Hz, 1H), 8.42 (dd, J=0.8, 3.2 Hz, 1H), 8.41-8.13 (m, 1H), 7.54-7.52 (m,1H), 7.47-7.43 (m, 1H), 7.23-7.17(m, 1H); $^{13}$C NMR (100 MHz, $d_6$-DMSO): δ 151.40, 145.52, 138.29, 127.80, 126.04, 120.59, 119.86, 118.85, 114.65, 114.40, 110.71. The reaction was shown as the following Equation (4).

Equation (4)

EXAMPLE C

Preparation of beta-carboline

Firstly, glyoxylic acid monohydrate (12.66 g, 137.6 mmol) was mixed with and dissolved in deionized water (30.00 mL). Tryptamine (20.0 g, 124.5 mmol) was also mixed and stirred with deionized water (380.00 mL), followed by adding several drops of hydrochloric acid. The two water solutions prepared as above were mixed and stirred for 15 minutes at room temperature, and a large amount of white precipitation was formed. In addition, a potassium hydroxide solution was prepared by dissolving potassium hydroxide (KOH, 6.8 g) in deionized water (34.00 mL). The potassium hydroxide solution was slowly added by drops into the mixed solution containing glyoxylic acid monohydrate and tryptamine, followed by adjusting the pH value of the solution to around 4 by hydrochloric acid. The mixture was stirred for one hour at room temperature and was allowed to stand in a freezer for 12 hours. After taken out from the freezer, the mixture was filtered by suction to collect solid, followed by added with deionized water (320.00 mL) and hydrochloric acid (60.00 mL). After refluxed for 30 minutes, the mixture was added with hydrochloric acid (60.00 mL) and refluxed again for 15 minutes, followed by cooling to room temperature. The mixture was allowed to stand in the freezer for two days for precipitation. The solid was collected and then added with deionized water. The mixture was heated to 165° C. to dissolve the solid and a dark green solution was formed. The pH value of the solution was adjusted to 12 by adding potassium hydroxide and a large amount of ligh green precipitation was formed. The solid was filtered by suction and the compound 3 (18.19 g) was obtained. The yield is 80%. Spectral data as follow: $^1$H NMR (400 MHz, $d_6$-DMSO) : δ 6 10.67 (s, 1H), 7.34 (d, J=7.6 Hz, 1H), 7.26 (d, J=8.0 Hz, 1H), 6.99 (m, 1H), 6.94-6.93 (m, 1H), 3.86 (s, 2H), 3.08 (br s, 2H), 2.98 (t, J=5.2 Hz, 2H), 2.59 (m, 2H) ; $^{13}$C NMR (100 MHz, $d_6$-DMSO) : δ 134.99, 133.68, 126.76, 119.67, 117.60, 116.64, 110.27, 106.42, 42.87, 42.14, 21.67. The reaction was shown as the following Equation (5).

Equation (5)

Next, the compound 3 (5.11 g, 29.7 mmol) was added with p-xylene (150.00 mL), reacted with the catalyst of palladium on carbon (Pd/C, 10% , 2.0 mg), and heated to 145° C. and refluxed for 48 hours, followed by cooling to room temperature. The mixture was filtered through celite and washed with methyl alcohol. The solvent was removed by using a rotary vacuum concentrator, and the compound 4 (beta-carboline, 2.48 g) of light yellow solid was obtained. The yield is 49.5%. Spectral data as follow: $^1$H NMR (400 MHz, $d_6$-DMSO) : δ 11.63 (s, 1H), 8.90 (s, 1H), 8.34 (d, J=4.0 Hz, 1H), 8.24 (d, J=8.0 Hz, 1H), 8.11 (d, J=0.8 Hz, 1H), 7.61-7.54 (m, 2H), 7.24 (m, 1H) ; $^{13}$C NMR (100 MHz, d$_6$-DMSO) : δ 140.00, 137.58, 135.46, 133.50, 127.57, 126.91, 121.26, 120.08, 114.11, 111.42. The reaction was shown as the following Equation (6).

Equation (6)

EXAMPLE D

Preparation of gamma-carboline 4-aminopyridine (2.832 g, 30.0 mmol), sodium tert-butoxide (3.420 g, 35.7 mmol), 1,1'-Bis(diphenylphosphino) ferrocene (600.0 mg, 1.1 mmol), and tris(dibenzylideneacetone)-dipalladium (411.0 mg, 0.5 mmol) were placed in a double neck flask (250 mL), and dry toluene (90.00 mL) was added under argon atmosphere. The mixture was heated to 145° C. and refluxed for 24 hours, followed by cooling to room temperature. The mixture was filtered through celite and washed with ether. After purified by column chromatography and eluted by the solution of dichloromethane and methyl alcohol (15:1 in v/v), the compound 5 (7.5 g) of light grey solid was obtained, and the yield is 95%. Spectral data as follow: $^1$H NMR (400 MHz, d$_6$-DMSO) : δ 8.47 (s, 1H), 8.17 (d, J=6.4 Hz, 2H), 7.72-7.70 (m, 1H), 7.42-7.39 (m, 2H), 7.15-7.13 (m, 1H), 6.71 (dd, J=1.2, 1.2 Hz, 2H) ; $^{13}$C NMR (100 MHz, d$_6$-DMSO) : δ 150.10, 149.20, 137.68, 132.83, 128.00, 125.73, 125.03, 108.43. The reaction was shown as the following Equation (7).

Equation (7)

Next, the compound 5 (7.5 g , 30.2 mmol), palladium(II) acetate (336.0 mg, 1.5 mmol), sodium carbonate (4.44 g, 42.0 mmol), and dimethylformamide (60.00 mL) were mixed and heated to 165° C. and refluxed for 24 hours, followed by cooling to room temperature. The mixture was filtered through celite and washed with ethyl acetate. Most of the ethyl acetate was removed by using a rotary vacuum concentrator. Sodium hydroxide was added to the solution directly until the solution was neutral. A black suspension was formed and the solution was filtered by suction to remove the suspension and to collect the filtrate. After continuously adding with sodium hydroxide, a large amount of white precipitation was formed. The mixture was filtered by suction and the white precipitation was collected. After washed by ether, the compound 6 (gamma-carboline) was obtained, and the yield is 50.89%. Spectral data as follow: $^1$H NMR (400 MHz, d$_6$-DMSO) : δ 11.71 (s, 1H), 9.33 (s, 1H), 8.42 (d, J=5.6 Hz, 1H), 8.23 (d, J=8.0 Hz, 1H), 7.57-7.55 (m,1H), 7.49-7.45 (m, 2H), 7.28-7.24 (m, 1H) ; $^{13}$C NMR (100 MHz, d$_6$-DMSO) : δ 203.10, 144.00, 143.00, 142.24, 139.01, 126.07, 120.20, 120.09, 119.45, 118.89, 110.95, 105.84. The reaction was shown as the following Equation (8).

Equation (8)

EXAMPLE E

Synthesis of the compound of Chemical Formula (1): 1-CbOXD

The compound 2 of yellow solid (0.5 g , 2.9 mmol), the compound 8 of white crystalized solid (1.0 g , 3.3 mmol), copper iodide (20.0 mg, 0.1 mmol), potassium carbonate (1.6 g, 11.9 mmol), and L-proline (27.0 mg, 0.2 mmol) were placed in a double neck flask (5.00 mL), and dimethyl sulfoxide (0.65 mL) was injected under argon atmosphere. The mixture was heated to 90° C. and refluxed for 48 hours, followed by cooling to room temperature. The mixture was filtered through celite, purified by column chromatography, and eluted by the solution of dichloromethane and ethyl acetate (4:1 in v/v). The solvent was removed by using a rotary vacuum concentrator, and the compound of Chemical Formula (1) (1-CbOXD, 0.97 g) of yellow solid was obtained. The yield is 84.2%. Spectral data as follow: $^1$H NMR (400 MHz, d$_6$-DMSO) : δ 8.64 (dd, J=1.4, 1.4 Hz, 1H), 8.43 (dd, J=1.7, 0.9 Hz, 1H), 8.34 (d, J=7.7 Hz, 1H), 8.25 (dd, J=1.4, 1.4 Hz, 1H), 7.96-7.92 (m, 1H), 7.86-7.83 (m, 2H), 7.48-7.43 (m, 2H), 7.34 (t, J=7.6 Hz, 3H), 7.25-7.22 (m, 1H), 7.20-7.16 (m, 3H) ;$^{13}$C NMR (100 MHz, d$_6$-DMSO) : δ 163.12, 161.85, 151.66, 145.96, 133.52, 133.10, 131.69, 130.87, 130.03, 129.32, 128.79, 127.09, 125.64, 122.45, 121.16, 120.58, 120.30, 116.04, 115.59, 109.44 ; HRMS m/z [M+Na]$^+$411.1216 o Anal. Calcd for $C_{44}H_{29}N_5$: C, 84.19; H, 4.66; N, 11.16; Found: C, 84.22; H, 4.70; N, 11.08. The reaction was shown as the following Equation (9).

Equation (9)

EXAMPLE F

Synthesis of the compound of Chemical Formula (2): 2-CbOXD

The compound 4 (0.5 g, 2.9 mmol), the compound 8 (1.0 g, 3.3 mmol), copper iodide (20.0 mg, 0.1 mmol), potassium carbonate (1.64g, 11.9 mmol), and L-proline (27.1 mg, 0.2 mmol) were placed in a double flask (5.00 mL), and dimethyl sulfoxide (0.65 mL) was injected under argon atmosphere. The mixture was heated to 90° C. and refluxed for 48 hours, followed by cooling to room temperature. The mixture was filtered through celite, purified by column chromatography, and eluted by the solution of dichloromethane and ethyl acetate (4:1 in v/v). The solvent was removed by using a rotary vacuum concentrator, and the compound of Chemical Formula (2) (2-CbOXD, 0.53 g) of yellow solid was obtained. The yield is 46.2%. Spectral data as follow: $^1$H NMR (400 MHz, $d_6$-DMSO) : δ 8.48-8.45 (m,3H), 8.45 (d, J=2.0 Hz, 1H), 8.26 (dd, J=1.2, 1.2 Hz, 1H), 8.00-7.96 (m, 1H), 7.93-7.88 (m, 2H), 7.51-7.44 (m, 2H), 7.36-7.30 (m, 3H), 7.16-7.10 (m, 3H) ; $^{13}$C NMR (100 MHz, $d_6$-DMSO) : δ 164.13, 162.19, 142.33, 140.26, 137.66, 134.45, 132.90, 132.51, 131.59, 131.37, 130.7, 129.56, 129.50, 128.80, 126.46, 122.98, 122.60, 121.56, 121.14, 115.31, 110.48. HRMS m/z [M+Na]$^+$411.1216. ○ Anal. Calcd for $C_{44}H_{29}N_5$: C, 84.19; H, 4.66; N, 11.16; Found: C, 84.22; H, 4.70; N, 11.08. The reaction was shown as the following Equation (10).

Equation (10)

EXAMPLE G

Synthesis of the compound of Chemical Formula (3): 3-CbOXD

The compound 6 (0.5 g, 2.9 mmol), the compound 8 (1.0 g, 3.3 mmol), copper iodide (20.0 mg, 0.1 mmol), potassium carbonate (1.64g, 11.9 mmol), and L-proline (27.1 mg, 0.2 mmol) were placed in a double flask (5.00 mL), and dimethyl sulfoxide (0.65 mL) was injected under argon atmosphere. The mixture was heated to 90° C. and refluxed for 48 hours, followed by cooling to room temperature. The mixture was filtered through celite, purified by column chromatography, and eluted by the solution of dichloromethane and ethyl acetate (4:1 in v/v). The solvent was removed by using a rotary vacuum concentrator, and the compound of Chemical Formula (3) (3-CbOXD, 0.53 g) of light brown solid was obtained. The yield is 47.6%. Spectral data as follow: $^1$H NMR (400 MHz, $d_6$-DMSO) : δ 8.49-8.43 (m, 3H), 8.02-7.87 (m, 3H), 7.50-7.35 (m, 6H), 7.24-7.12 (m, 4H) ; $^{13}$C NMR (100 MHz, $d_6$-DMSO): δ 163.13, 160.95, 145.03, 143.00, 140.96, 133.50, 132.42, 131.58, 130.46, 130.29, 130.16, 128.60, 127.41, 125.51, 121.85, 121.24, 120.78, 120.44, 119.25, 109.55, 104.82. HRMS m/z [M+Na]$^+$ 411.1216 ○ Anal. Calcd for $C_{44}H_{29}N_5$: C, 84.19; H, 4.66; N, 11.16; Found: C, 84.22; H, 4.70; N, 11.08. The reaction was shown as the following Equation (11).

Equation (11)

-continued

Evaluation Methods for the Host Material

The host material includes the compound which is mentioned above from Example E to Example G (i.e., Chemical Formula (1) to Chemical Formula (3)). The evaluation methods for the host material is to perform the measurements of the triplet energy gap ($E_T$), the glass transition temperature ($T_g$), the pyrolysis temperature ($T_d$), the highest occupied molecular orbital energy gap (HOMO), and the lowest unoccupied molecular orbital energy gap (LUMO) on above mentioned compound of examples, respectively. The triplet energy gap measured at low temperature by spectrometer is the basis of selecting the host material of phosphorescent luminary. For blue light-emitting diode, FIrpic ($E_T$=2.65 eV) is a common phosphorescent luminary and the $E_T$ of the host luminary developed by FIrpic should be higher than 2.65 eV to avoid back energy transfer which results in reducing luminous efficiency. The glass transition temperature and the pyrolysis temperature respectively measured by differential scanning calorimeter (DSC) and thermogravimetric analyzer (TGA) is considered to be the basis of the stability for the fabrication and performance of unit. HOMO and LUMO are acquired receptively from oxidation potential and reduction potential of the material by using cyclic voltammetry, which can facilitate in searching of an electron injection material with small difference energy gap and enhance the efficiency of the unit. The properties of the compounds of Chemical Formula (1) (1-CbOXD), Chemical Formula (2) (2-CbOXD), and Chemical Formula (3) (3-CbOXD) are shown in Table 1.

TABLE 1

| Compound | $E_T$ (eV) | $T_g$ (° C.) | $T_d$ (° C.) | HOMO (eV) | LUMO (eV) |
|---|---|---|---|---|---|
| Chemical Formula (1) | 3.30 | 53 | 266 | −5.88 | −2.58 |
| Chemical Formula (2) | 3.30 | 53 | 269 | −5.90 | −2.60 |
| Chemical Formula (3) | 3.27 | 57 | 319 | −5.93 | −2.66 |

According to Table 1, the pyrolysis temperatures of the compounds of Chemical Formula (1) (1-CbOXD), Chemical Formula (2) (2-CbOXD) and Chemical Formula (3) (3-CbOXD) are all higher than 200° C. It is because that their structures contain multiple benzene rings which are rigid structures, so that the pyrolysis caused by the heat is not easily occurred during the heating process. Based on the reason mentioned above, their derivatives have fine heat stability and high triplet energy gap and are quite beneficial to be the host material in organic luminescent layer of organic light emitting diode.

The Efficiency of Compound (Chemical Formula (1), 1-CbOXD, Chemical Formula (2), 2-CbOXD, and Chemical Formula (3), 3-CbOXD) as Host Material in Organic Light Emitting Diode The unit structure is ITO/TAPC(50 nm)/mCP(10 nm)/host: emitter(30 nm)/DPPS(30 nm)/LiF(0.9 nm)/Al(120 nm). The host material of the organic luminescent layer is based on the compound of Chemical Formula (1), Chemical Formula (2) or Chemical Formula (3). The host material mixes with the guest material at various ratio of emitter (FIrpic). Here, the material of first electrode layer of the organic electroluminescent device is ITO. The material of the second electrode layer is aluminum with the thickness of 120 nm. The material of the hole transport layer is TAPC with the thickness of 50 nm. The thickness of the organic luminescent layer is 30 nm. The material of the electron blocking layer is mCP with the thickness of 10 nm. The material of the electron transport layer is DPPS with the thickness of 30 nm. The material of electron injecting layer is LiF with the thickness of 0.9 nm. The organic electroluminescent devices are made by vapor deposition to form the above-mentioned layers, and the driving voltage (V) under the luminance of 1000 cd/m², the maximum current efficiency (cd/A), the maximum power efficiency (lm/W), and the maximum external quantum efficiency (EQE) (%) of the organic electroluminescent devices are measured. The results are shown in Table 2.

TABLE 2

| unit[a] | driving voltage (V) [b] | maximum current efficiency (cd/A) | maximum power efficiency (lm/W) | EQE (%) |
|---|---|---|---|---|
| Chemical Formula (1) −12% | 6.65 | 49.31@4.5 V | 37.55@4 V | 22.03 |
| Chemical Formula (2) −12% | 6.76 | 46.92@4.5 V | 33.87@4 V | 22.89 |
| Chemical Formula (3) −6% | 7.41 | 48.99@4.5 V | 36.24@4 V | 23.43 |

[a] The doping concentration of FIrpic
[b] the unit of operation voltage under the luminance of 1000 cd/m²

The organic electroluminescent devices shown in Table 2 not only have low driving voltages but also have the fine current efficiency, power efficiency and external quantum efficiency. Accordingly, the host materials of the present invention have high transmission rate of electrons and holes, and are not necessarily to be operated under high driving voltage. Also, the external quantum efficiencies of the host materials shown in Table 2 are high as well. Consequently, the host materials of the present invention have higher triplet energy gap, which is beneficial to reduce back energy transfer and to increase the luminous efficiency of organic electroluminescent device.

In summary, the organic electroluminescent materials containing N-phenylcarboline and the organic electroluminescent device by using the same are based on the N-phenylcarboline group and the oxadiazole group. In addition, the N-phenylcarboline group is undergone single nitrogen-substituted heterocyclic ring modification, and the positions of the nitrogen-substitution are various. Therefore, the phosphorescent dipolar host materials, such as 1-CbOXD, 2-CbOXD, and 3-CbOXD, are synthesized accordingly. In the present invention, the carboline group is functioned as a hole-transporting group, and the oxadiazole group is functioned as an electron-transporting group, and the hole-transporting group is undergone single nitrogen-substituted heterocyclic ring modification. Therefore, the phosphorescent dipolar host materials are synthesized accordingly. Such phosphorescent dipolar host materials and the organic light-emitting diodes comprising such materials will have high luminous efficiency.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An organic electroluminescent material, comprising a structure of the following General Formula (1), General Formula (1)

whererin one of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

2. The organic electroluminescent material of claim 1, wherein the alkyl group is selected from the group consisting of a substituted or unsubstituted straight-chain alkyl group with the carbon number of 1 to 6, and a substituted or unsubstituted branched-chain alkyl group with the carbon number of 1 to 6, the cycloalkyl group is a substituted or unsubstituted cycloalkyl group with the carbon number of 1 to 6,the alkoxy group is selected from the group consisting of a substituted or unsubstituted straight-chain alkoxy group with the carbon number of 1 to 6, and a substituted or unsubstituted branched-chain alkoxy group with the carbon number of 1 to 6, thioalkyl group is selected from the group consisting of a substituted or unsubstituted straight-chain thioalkyl group with the carbon number of 1 to 6, a substituted or unsubstituted branched-chain thioalkyl group with the carbon number of 1 to 6, the silyl group is selected from the group consisting of a substituted or unsubstituted straight-chain silyl group with the carbon number of 1 to 6, and a substituted or unsubstituted branched-chain silyl group with the carbon number of 1 to 6, and the alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

3. The organic electroluminescent material of claim 1, wherein X1 is a nitrogen atom, X2 and X3 are both independent carbon atoms, and R1 to R14 are all independent hydrogen atoms.

4. The organic electroluminescent material of claim 1, wherein X2 is a nitrogen atom, X1 and X3 are both independent carbon atoms, and R1 to R14 are all independent hydrogen atoms.

5. The organic electroluminescent material of claim 1, wherein X3 is a nitrogen atom, X1 and X2 are both independent carbon atoms, and R1 to R14 are all independent hydrogen atoms.

6. An organic electroluminescent device, comprising:
a first electrode layer;
a second electrode layer; and
an organic luminescent unit, disposed between the first electrode layer and the second electrode layer, wherein the organic luminescent unit has at least an organic luminescent material as shown in General Formula (1), General Formula (1)

wherein one of X1, X2, and X3 is an independent nitrogen atom, and R1 to R14 are each independently selected from the group consisting of a hydrogen atom, a fluorine atom, a cyano group, an alkyl group, a cycloalkyl group, an alkoxy group, a thioalkyl group, a silyl group, and an alkenyl group.

7. The organic electroluminescent device of claim 6, wherein the organic luminescent unit comprises an organic luminescent layer.

8. The organic electroluminescent device of claim 7, wherein the organic luminescent unit further comprises a hole transport layer and an electron transport layer, and the organic luminescent layer is disposed between the hole transport layer and the electron transport layer.

9. The organic electroluminescent device of claim 7, wherein the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

10. The organic electroluminescent device of claim 7, wherein the organic luminescent layer comprises a host material and a guest material, and the host material is the organic electroluminescent material and the guest material is a phosphorescent material.

11. The organic electroluminescent device of claim 10, wherein the content of the host material in the organic luminescent layer is between 60 vol % to 95 vol %.

12. The organic electroluminescent device of claim 10, wherein the content of the guest material in the organic luminescent layer is between 5 vol % to 40 vol %.

* * * * *